(12) United States Patent
Marik et al.

(10) Patent No.: US 7,637,955 B2
(45) Date of Patent: Dec. 29, 2009

(54) CONSTRAINED ARTIFICIAL SPINAL DISC

(75) Inventors: Greg Marik, Germantown, TN (US);
Kevin Foley, Germantown, TN (US);
Tom Francis, Cordova, TN (US);
Randall Allard, Germantown, TN (US)

(73) Assignee: Warsaw Orthopedic, Inc.

(*) Notice: Subject to any disclaimer, the term of this patent is extended or adjusted under 35 U.S.C. 154(b) by 82 days.

(21) Appl. No.: 10/806,961

(22) Filed: Mar. 23, 2004

(65) Prior Publication Data

US 2005/0216086 A1 Sep. 29, 2005

(51) Int. Cl.
*A61F 2/44* (2006.01)

(52) U.S. Cl. .................... 623/17.14; 623/17.15

(58) Field of Classification Search ..... 623/23.39–24.1, 623/20.22, 19.12, 23.4, 22.42, 22.16, 17.11–17.16, 623/21.11–21.19, 18.11
See application file for complete search history.

(56) References Cited

U.S. PATENT DOCUMENTS

| | | | | |
|---|---|---|---|---|
| 3,916,451 A | * | 11/1975 | Buechel et al. | 623/23.4 |
| 5,314,485 A | * | 5/1994 | Judet | 623/21.13 |
| 5,336,267 A | * | 8/1994 | Kubein-Meesenburg et al. | 623/23.39 |
| 5,360,449 A | * | 11/1994 | Branemark | 623/23.39 |
| 5,507,816 A | | 4/1996 | Bullivant | |
| 5,507,821 A | * | 4/1996 | Sennwald et al. | 623/21.13 |
| 5,534,029 A | * | 7/1996 | Shima | 623/17.15 |
| 5,556,431 A | * | 9/1996 | Buttner-Janz | 623/17.15 |
| 5,676,701 A | * | 10/1997 | Yuan et al. | 623/17.15 |
| 5,895,428 A | * | 4/1999 | Berry | 623/17.15 |
| 5,899,941 A | * | 5/1999 | Nishijima et al. | 623/17.15 |
| 6,146,421 A | * | 11/2000 | Gordon et al. | 623/17.15 |
| 6,179,874 B1 | * | 1/2001 | Cauthen | 623/17.14 |
| 6,368,350 B1 | | 4/2002 | Erickson et al. | |
| 7,048,764 B2 | * | 5/2006 | Ferree | 623/17.15 |
| 7,066,958 B2 | * | 6/2006 | Ferree | 623/17.12 |
| 2002/0082701 A1 | * | 6/2002 | Zdeblick et al. | 623/17.16 |
| 2003/0045939 A1 | * | 3/2003 | Casutt | 623/17.15 |
| 2003/0208280 A1 | * | 11/2003 | Tohidi | 623/23.39 |
| 2004/0002761 A1 | | 1/2004 | Rogers et al. | |
| 2004/0030391 A1 | * | 2/2004 | Ferree | 623/17.16 |

(Continued)

FOREIGN PATENT DOCUMENTS

EP 0 560 141 9/1993

(Continued)

OTHER PUBLICATIONS

T. Hoogland et al., "Total Lumbar Intervertebral Disc Replacement: Testing of a New Articulating Spacer in Human Cadaver Spines," 24th Annual ORS, Feb. 21-23, 1978, p. 102, Dallas, Texas.

(Continued)

*Primary Examiner*—Corrine McDermott
*Assistant Examiner*—Cheryl Miller

(57) ABSTRACT

An intervertebral implant comprises a first member for engaging a first vertebral body and a second member for engaging a second vertebral body. The first member has a first surface with a first curve, and the second member has a second surface with a second curve. The first member is translatable with respect to the second member and the second curve is positioned within the first curve to bias the first and second curved surfaces towards central alignment along a longitudinal axis passing through the first and second vertebral bodies.

17 Claims, 6 Drawing Sheets

U.S. PATENT DOCUMENTS

| | | | |
|---|---|---|---|
| 2004/0133278 A1* | 7/2004 | Marino et al. | 623/17.14 |
| 2004/0133281 A1* | 7/2004 | Khandkar et al. | 623/17.16 |
| 2004/0143332 A1* | 7/2004 | Krueger et al. | 623/17.14 |
| 2005/0187633 A1* | 8/2005 | Ferree | 623/17.15 |
| 2005/0216092 A1* | 9/2005 | Marik et al. | 623/23.39 |
| 2006/0036325 A1* | 2/2006 | Paul et al. | 623/17.14 |
| 2006/0116768 A1* | 6/2006 | Krueger et al. | 623/17.14 |
| 2006/0259144 A1* | 11/2006 | Trieu | 623/17.13 |
| 2008/0183296 A1* | 7/2008 | Ferree | 623/17.16 |
| 2008/0234686 A1* | 9/2008 | Beaurain et al. | 606/90 |

FOREIGN PATENT DOCUMENTS

| | | | |
|---|---|---|---|
| EP | 1 374 808 A1 | 1/2004 | |
| FR | 2 730 159 | 8/1996 | |
| FR | 2 730 159 A1 | 8/1996 | |
| WO | WO 00/23015 | 4/2000 | |
| WO | WO 02/089701 | 11/2002 | |
| WO | WO/02089701 | 11/2002 | |
| WO | WO 2004/002291 | 1/2004 | |

OTHER PUBLICATIONS

European Patent Office, International Searching Authority, "PCT Notification of Transmittal of The International Search Report and The Written Opinion of the International Searching Authority, or the Declaration," International Application No. PCT/US2005/009755, Jul. 25, 2005, 15 pages.

European Patent Office, International Searching Authority, "PCT Notification of Transmittal of The International Search Report and The Written Opinion of the International Searching Authority, or the Declaration," International Application No. PCT/US2005/009777, Jul. 26, 2005, 19 pages.

* cited by examiner

CONSTRAINED ARTIFICIAL SPINAL DISC

BACKGROUND

During the past thirty years, technical advances in the design of large joint reconstructive devices has revolutionized the treatment of degenerative joint disease, moving the standard of care from arthrodesis to arthroplasty. Progress in the treatment of vertebral disc disease, however, has come at a slower pace. Currently, the standard treatment for disc disease remains discectomy followed by vertebral fusion. While this approach may alleviate a patient's present symptoms, accelerated degeneration of adjacent discs is a frequent consequence of the increased motion and forces induced by fusion. Thus, reconstructing the degenerated intervertebral disc with a stable, functional disc prosthesis to provide motion and to reduce deterioration of the adjacent discs may be a more desirable treatment option for many patients.

SUMMARY

In one embodiment, an intervertebral implant comprises a first member for engaging a first vertebral body and a second member for engaging a second vertebral body. The first member has a first surface with a first curve, and the second member has a second surface with a second curve. The first member is translatable with respect to the second member and the second curve is positioned within the first curve to bias the first and second curved surfaces towards central alignment along a longitudinal axis passing through the first and second vertebral bodies.

DETAILED DESCRIPTION

Figure 1:
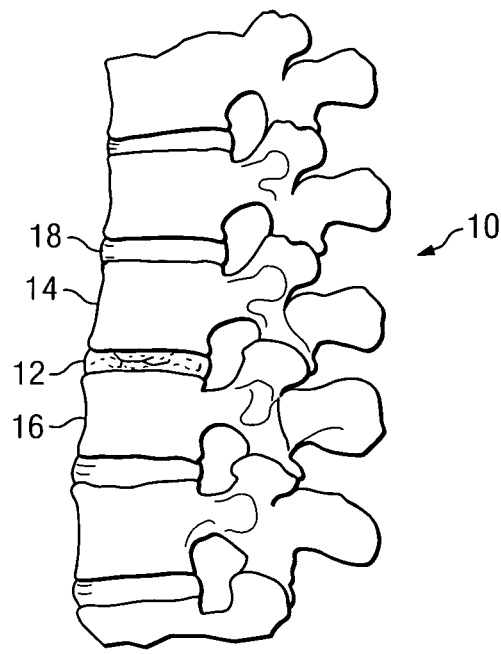
FIG. 1 is a sagittal view of a vertebral column having a damaged disc.

The present disclosure relates generally to the field of orthopedic surgery, and more particularly to an apparatus and method for vertebral reconstruction using a functional intervertebral prosthesis. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the invention relates.

Referring first to FIG. 1, the numeral 10 refers to vertebral column with a damaged intervertebral disc 12 extending between vertebrae 14 and 16. In a typical surgical discectomy, the disc 12 is removed, creating a void between the two intact vertebrae 14 and 16. This procedure may be performed using an anterior, anterolateral, lateral, or other approach known to one skilled in the art. An implant according to an embodiment of the present invention may then be provided to fill the void between the two intact vertebrae 14 and 16. The embodiments disclosed may be used in the cervical, thoracic, or lumbar spine or in other regions of the vertebral column. Although the embodiments to be described are generally premised upon the removal of a single disc, it is understood that more than one of the disclosed devices may be used in a multi-level disc replacement such as, for example, the replacement of disc 12 and a disc 18. The methods and apparatus of this disclosure may also be applied to the insertion of a vertebral body replacement device between two vertebrae following a corpectomy, in which at least one vertebral body has been removed. Moreover, the methods and apparatus of this disclosure may also be applied in any of a variety of applications in which motion preservation is needed or desired.

Figure 2:
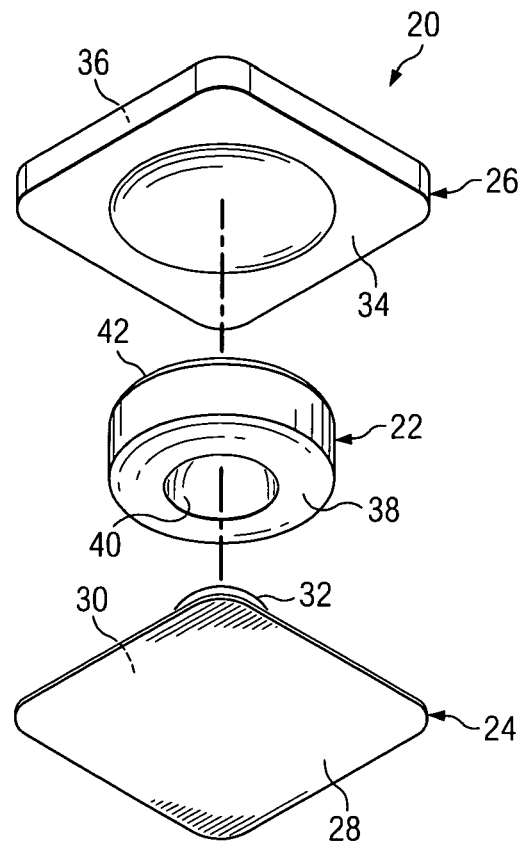
FIG. 2 is an exploded intervertebral assembly according to a first embodiment of the current disclosure.

Referring now to FIG. 2, a joint prosthesis 20, which in this embodiment may be an intervertebral disc prosthesis, includes a center member 22 interposed between two endplate assemblies 24, 26. The endplate assembly 24 may include an exterior surface 28 and an interior surface 30. An articulation mechanism such as a protrusion 32 may extend from the interior surface 30. In this embodiment the protrusion may be semi spherical, however protrusions may be provided in a variety of shapes, a few of which will be described in other embodiments. The surfaces 28 and 30 may be flat, angled, or curved. In this embodiment, the exterior surface 28 may be relatively flat or may be contoured to match the surface of an adjacent vertebral endplate. The interior surface 30 may taper away from or towards the protrusion 32.

The endplate assembly 26 may include a interior surface 34 and an exterior surface 36. The surfaces 34 and 36 may be flat, angled, or curved. In this embodiment, the surface 36 may be generally flat or may be contoured to match the surface of an adjacent vertebral endplate. The exterior surface 36 may include features (not shown), such as fins or keels, to secure the prosthesis 20 to the adjacent bone. The interior surface 34 may be generally concave and may serve as an articulation mechanism.

The center member 22 may vary somewhat in shape, size, composition, and physical properties, depending upon the particular joint for which the implant is intended or a particular deformity which the prosthesis 20 is intended to correct. The shape of the center member 22 may complement that of the interior surfaces 30, 34 of the endplate assemblies 24, 26 to allow for a range of translational, flexural, extensional, rotational, and lateral bending motion appropriate to the particular joint being replaced. In this embodiment, the center member 22 may include a surface 38 having a cavity 40 generally conforming to the shape of the protrusion 32. The center member 22 may also have a surface 42 which, in this embodiment, may generally conform to the shape of the interior surface 34.

The endplate assemblies 24, 26 and center member 22 may be formed of any suitable biocompatible material including, cobalt-chrome alloys, stainless steel, titanium alloys, alumina, zirconia, polycrystalline diamond, pyrolytic carbon, polyetheretherketone (PEEK), ultra-high molecular weight polyethylene (UHMWPE), cross-linked UHMWPE, or other suitable materials. The surfaces 28, 36 may include features or coatings which enhance the purchase or ingrowth qualities of the implanted prosthesis. For example, a biocompatible and osteoconductive material such as hydroxyapatite (HA) may coat all or a portion of the surface 28. Other suitable coatings or treatments may include a porous bead coating, a porous mesh coating, osteogenic peptide coating, growth factor coating, rh-BMP coating, and/or grit blasting. Other suitable features may include serrations, spikes, ridges, fins, and/or other surface textures.

In some embodiments, the center member 22 may be formed of the relatively rigid materials listed above, and in other embodiments, the center member may permit a degree of elasticity or dampening, and accordingly, an elastomeric material may be used for the center member. Although the center member 22 may have a degree of flexibility, it may also be sufficiently stiff to effectively cooperate with the endplate assemblies to limit motion beyond an allowable range. The surface of the center member 22 may also be sufficiently durable to provide acceptable wear characteristics. In one embodiment, this combination of properties may be achieved with a center member 22 having surface regions that are harder than the material of the central body closer to its core. The portion 22 may, therefore, comprise a biocompatible composite or elastomeric material having a hardened surface.

Figure 3:
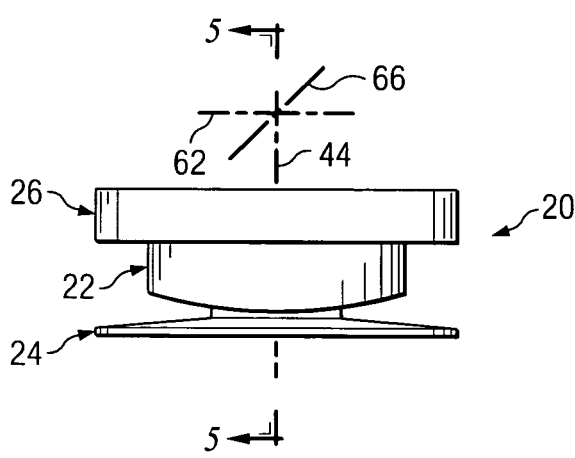
FIG. 3 is an assembled intervertebral assembly according to the first embodiment of the current disclosure.

Referring now to FIG. 3, the components of the intervertebral disc prosthesis 20 may be assembled by engaging the protrusion 32 with the cavity 40 and by positioning the surface 42 of the center member on the surface 34 of the endplate assembly 26. The components 26, 22, 24 may be centrally aligned along a longitudinal axis 44.

Figure 4:
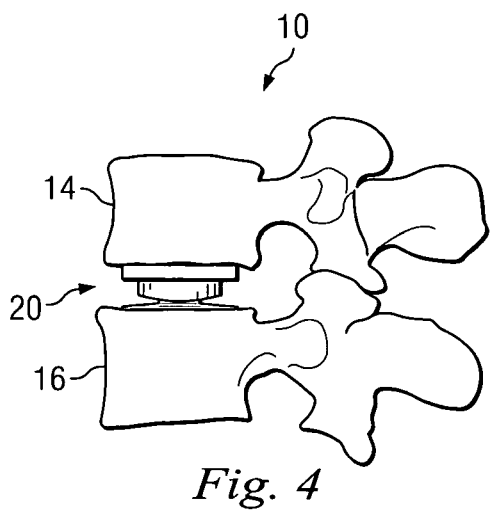
FIG. 4 is a sagittal view of a vertebral column implanted with the intervertebral assembly according to the first embodiment of the current disclosure.

Referring now to FIG. 4, the intervertebral disc prosthesis 20 may be inserted in the void of the vertebral column 10 (of FIG. 1) created by the removal of disc 12. In one embodiment, the surface 36 may contact an endplate of vertebra 14 and the surface 28 may contact the endplate of vertebra 16. In other embodiments, the prosthesis may be inverted.

Figure 5:
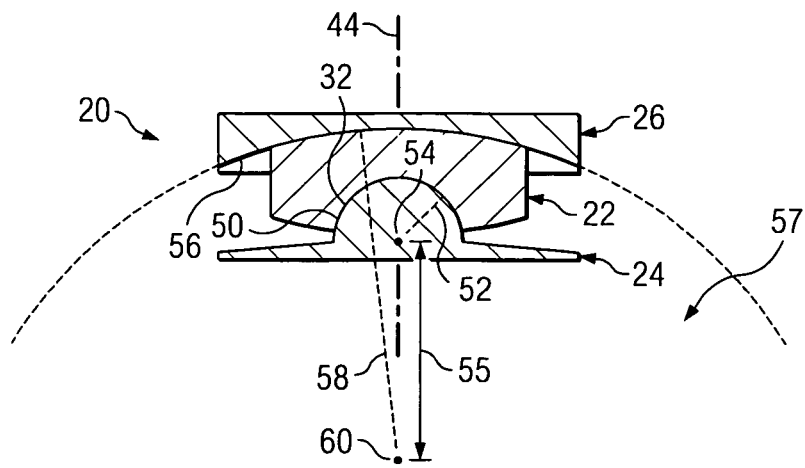
FIG. 5 is a cross sectional view of the assembled intervertebral assembly according to the first embodiment of the current disclosure.

As shown in the cross sectional view of FIG. 5, the intervertebral disc prosthesis 20 may be in a neutral position when the components 26, 22, 24 are centrally aligned along the longitudinal axis 44. The protrusion 32 may have a curve 50, which in this embodiment may be an arc with a relatively constant radius 52 and a center point 54. The surface 34 may have a curve 56 which in this embodiment may be an arc with a relatively constant radius 58 and a center point 60. A distance 55 may be measured between the center points 54, 60. In this example, the radius 52 is smaller than the radius 58, and accordingly, the arc 50 is tighter than the arc 56. In the neutral position, the center points 54 and 60 may be aligned along the longitudinal axis 44, and the smaller curve 50 may be positioned within the curve 56, which in this embodiment may be the area 57 defined by the sweep of the radius 58. As shown, the upper surface of the center member 22 complements the interior surface 34 of endplate assembly 26 such that the upper surface of the center member 22 has a radius of curvature substantially similar to radius 58 of the interior surface 34. Further, as shown, the lower surface 38 of the center member 22 surrounding the cavity 40 has a radius of curvature substantially similar to or equal to the upper surface of the center member 22, but in an opposite direction.

Figure 6:
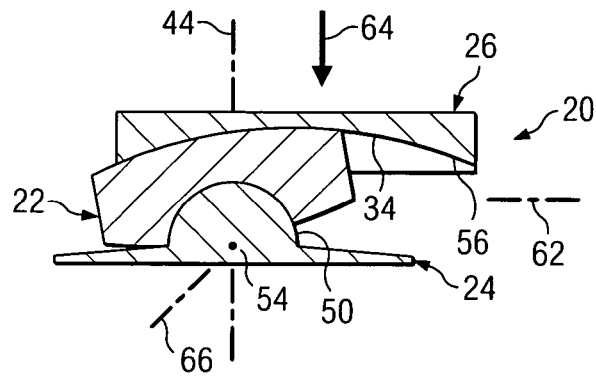
FIG. 6 is a cross sectional view of the translated intervertebral assembly according to the first embodiment of the current disclosure.

FIG. 6 shows the intervertebral disc prosthesis 20 in a translated position along, for example, an anterior-posterior axis 62. Translation may, for example, occur with flexion-extension movement. As the endplate assemblies 24, 26 are moved out of alignment relative to the axis 44, the center member 22 may articulate between the endplate assembly interior surfaces 30, 34. With the patient's body weight as a load 64 in the longitudinal direction 44 and the position of the smaller curve 50 within the larger curve 56, the prosthesis 20 may be biased to return to the more stable, neutral position in which the curves 50, 56 are aligned along the longitudinal axis 44. In this embodiment alignment may occur when the center points 54, 60 are aligned along the longitudinal axis 44. This embodiment describes curves which represent arcs of a circle, but in alternative embodiments the curves may be portions of other curves, such as an arc of an ellipse. In these alternative embodiments, alignment may occur when foci, for example of an ellipse, are in alignment or when center lines bisecting the curves are in alignment.

This tendency of the prosthesis 20 to self correct a spondylolisthesis or other displacement may allow freer, more natural joint movement while preventing excessive translation that could otherwise result in instability of the prosthesis 20.

Instability may result in the placement of unsustainable loads on adjacent joints or may result in the disassembly of the prosthesis 20. The alignment bias of the prosthesis 20 may relieve excessive loads that might otherwise form in adjacent joints due to chronic over-displacement of the endplate assemblies 24, 26. Although the wider arc is superior to the tighter arc in the orientation of this embodiment, in another embodiment, the orientation may be inverted with the tighter arc superior to the wider arc but with the tighter arc still falling within the curve of the wider arc.

It may be appreciated that the amount of alignment bias, and accordingly the amount of stability, may be related to the distance 55 between the center points 54, 60. As the distance 55 increases (for example, a sphere on a flat surface), stability, the amount of constraint within the prosthesis 20, and the tendency to self-align may decrease. As the distance 55 decreases (for example, a sphere in a tight socket), stability, constraint within the prosthesis 20, and the tendency to self-align may increase. Although this embodiment has been described as contemplating a displacement in the anterior-posterior direction 62, displacements caused by translation, bending, and/or rotation in other directions or combinations of directions may be corrected using other embodiments of the invention. For example, displacement of the endplate assembly 26 relative to the endplate 24 in a lateral direction 66 may also generate constraining forces which drive the center points 54, 60 back into alignment. The components 22-26 may be selected from a kit which allows the surgeon to design a patient specific prosthesis having a patient-appropriate amount of constraint and bias.

In embodiments involving multi-level disc removal, ligaments and other supportive soft tissue structures may be surgically removed or compromised. In these embodiments, replacing the discs with assemblies, such as prostheses 20, may resupply at least some of the stability lost with the removal of the soft tissue. This restored stability may prevent excessive loading and wear in the adjacent joints and may encourage more kinematically accurate motions.

Figure 7:
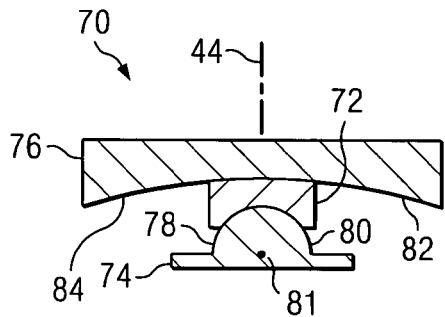
FIG. 7 is a cross sectional view of an assembled intervertebral assembly according to a second embodiment of the current disclosure.

Referring now to FIG. 7, in this embodiment, an intervertebral disc prosthesis 70, may include a center member 72 interposed between two endplate assemblies 74, 76. The endplate assembly 74 may include a protrusion 78 having a curve 80. In this embodiment, the curve 80 may be an arc having a centerpoint 81 and a constant radius. The endplate assembly 76 may include an interior surface 82 which may have a curve 84. In this embodiment, the curve 84 may be an arc having a center point 86 and a constant radius.

Figure 8:
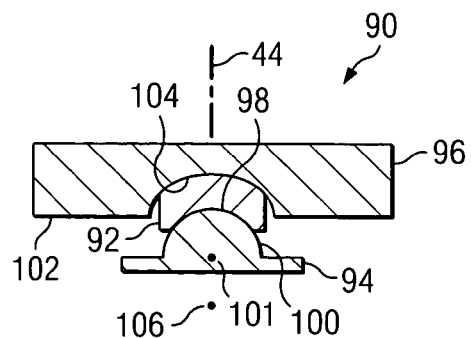
FIG. 8 is a cross sectional view of an assembled intervertebral assembly according to a third embodiment of the current disclosure.

Referring now to FIG. 8, in this embodiment, an intervertebral disc prosthesis 90, may include a center member 92 interposed between two endplate assemblies 94, 96. The endplate assembly 94 may include a protrusion 98 having a curve 100. In this embodiment, the curve 100 may be an arc having a center point 101 and a constant radius. The endplate assembly 96 may include an interior surface 102 which may have a curve 104. In this embodiment, the curve 104 may be an arc having a center point 106 and a constant radius.

The materials, the assembly, and the operation of prosthesis 90 may be similar to prosthesis 20 and therefore will not be described in detail. The shape of a protrusions relative to the shape of the contacted interior surfaces may correspond to the amount of constraint within the prosthesis. For example, where the arc-shaped curve 84 is wide compared to the relatively tight curve 104 in FIG. 7, the prosthesis 70 may be more constrained than prosthesis 90 in the embodiment of FIG. 8 wherein the arc-shaped curve 104 more closely matches the curve 100. Increased constraint may correspond to an increased bias for the prosthesis to return to the neutral position with the center points centrally aligned about the longitudinal axis 44.

Figure 9:
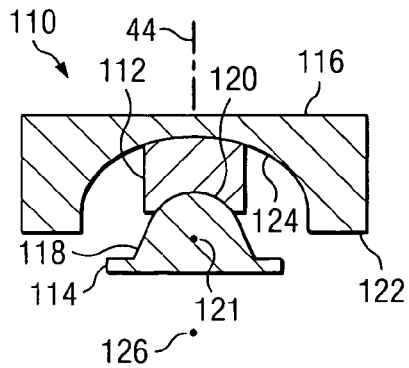
FIG. 9 is a cross sectional view of an assembled intervertebral assembly according to a fourth embodiment of the current disclosure.

Referring now to FIG. 9, in this embodiment, an intervertebral disc prosthesis 110, may include a center member 112 interposed between two endplate assemblies 114, 116. The endplate assembly 114 may include a protrusion 118 having a curve 120. In this embodiment, the curve 120 may be a semi-ellipse or other type of curved arc having a focus point 121 and a variable radius. The endplate assembly 116 may include an interior surface 122 which may have a curve 124. In this embodiment, the curve 124 may be U-shaped having a focus point 126, a variable radius, angled flat, and/or parallel flat portions. The materials and the assembly of prosthesis 110 may be similar to prosthesis 20 and therefore will not be described in detail. In operation, the prosthesis 110 may be biased toward alignment of the foci 121, 126 about the longitudinal axis 44.

Figure 10:
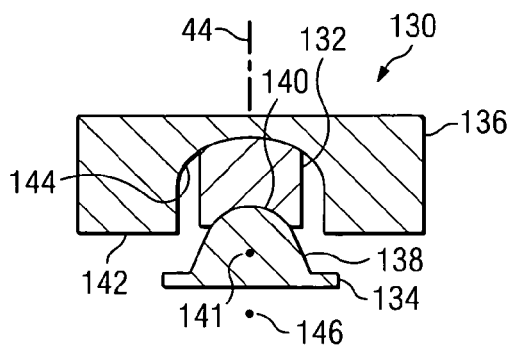
FIG. 10 is a cross sectional view of an assembled intervertebral assembly according to a fifth embodiment of the current disclosure.

Referring now to FIG. 10, in this embodiment, an intervertebral disc prosthesis 130, may include a center member 132 interposed between two endplate assemblies 134, 136. The endplate assembly 134 may include a protrusion 138 having a curve 140. In this embodiment, the curve 140 may be a semi-ellipse having a focus point 141 and a variable radius. The endplate assembly 136 may include an interior surface 142 which may have a curve 144. In this embodiment, the curve 144 may be U shaped having a focus point 146, a variable radius, angled flat, and/or parallel flat sections.

The materials and the assembly of prostheses 110, 130 may be similar to prosthesis 20 and therefore will not be described in detail. In operation, the prosthesis 130 may be biased toward alignment of the foci 141, 146 about the longitudinal axis 44. As shown in FIGS. 9 and 10, in some embodiments, the shape of the curves 124, 144 may not correspond to constant radius arcs of a circle, but rather the shape of the curve may be, for example, a U-shape, a semi-ellipse, or an elliptic curve. In FIG. 9 where the U-shaped curve 124 is wide compared to the relatively tight curve 144 of FIG. 10, the prosthesis 110 may be less constrained than prosthesis 130 wherein the U-shaped curve 154 is relatively tight and more closely matches the curve 140. It may be appreciated that the prosthesis 110 (FIG. 9) may be more constrained than prosthesis 70 (FIG. 7) as the walls of the U-shape may increase the bias for the prosthesis 110 to return to the neutral position.

Figure 11:
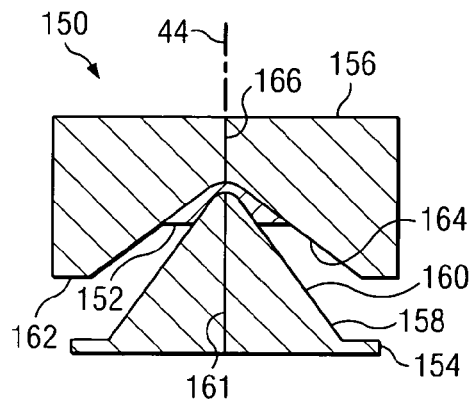
FIG. 11 is a cross sectional view of an assembled intervertebral assembly according to a sixth embodiment of the current disclosure.

Referring now to FIG. 11, in this embodiment, an intervertebral disc prosthesis 150, may include an center member 152 interposed between two endplate assemblies 154, 156. The endplate assembly 154 may include a protrusion 158 having a curve 160. In this embodiment, the curve 160 may have a combination of curved and flat surfaces and may have a center line 161 bisecting the curve 160. The endplate assembly 156 may include an interior surface 162 which may have a curve 164. In this embodiment, the curve 164 may have a combination of curved and flat surfaces and may have a center line 166 bisecting the curve 164. The materials and the assembly of prosthesis 150 may be similar to prosthesis 20 and therefore will not be described in detail. In operation, the prosthesis 150 may be biased toward alignment of the center lines 161, 166 along the axis 44.

Figure 12:
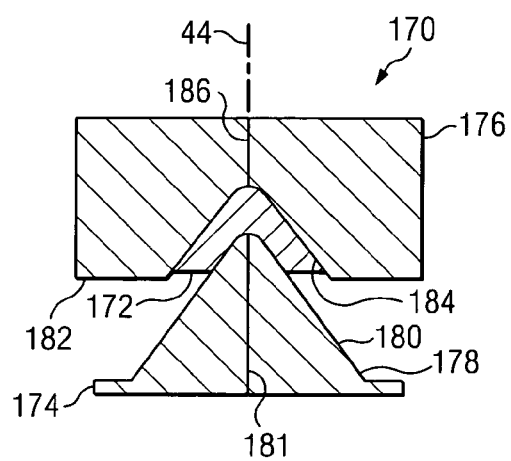
FIG. 12 is a cross sectional view of an assembled intervertebral assembly according to a seventh embodiment of the current disclosure.

Referring now to FIG. 12, in this embodiment, an intervertebral disc prosthesis 170, may include an center member 172 interposed between two endplate assemblies 174, 176. The endplate assembly 174 may include a protrusion 178 having a curve 180. In this embodiment, the curve 180 may have a combination of curved and flat surfaces and may have a center line 181 bisecting the curve 180. The endplate assembly 176 may include an interior surface 182 which may have a curve 184. In this embodiment, the curve 184 may have a combination of curved and flat surfaces and may have a center line 186 bisecting the curve 180. The materials, the assembly, and the operation of prosthesis 170 may be similar to prosthesis 20 and therefore will not be described in detail.

For prostheses 150, 170, the curves 164, 184 are relatively pointed compared to curve 80 (FIG. 7). In FIG. 11 where the pointed curve 164 is wide compared to the relatively tight curve 184 of FIG. 12, the prosthesis 150 may be less constrained than prosthesis 170 wherein the U-shaped curve 184 is relatively tight and more closely matches the curve 180.

Figure 13:
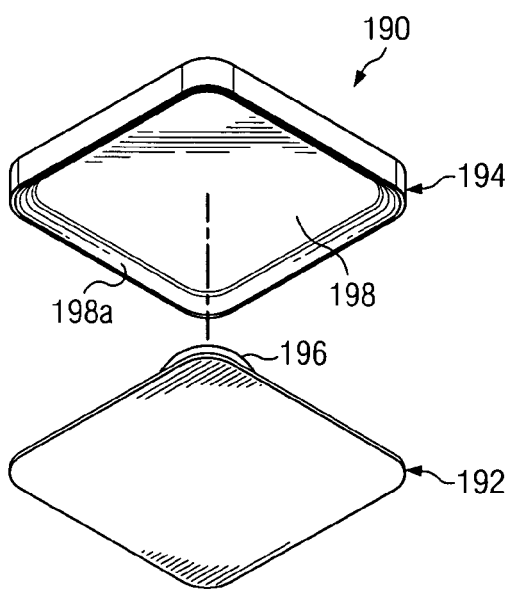
FIG. 13 is an exploded intervertebral assembly according to an eighth embodiment of the current disclosure.
Figure 14:
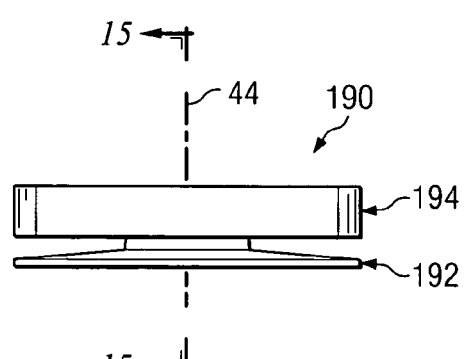
FIG. 14 is an assembled intervertebral assembly according to the eighth embodiment of the current disclosure.
Figure 15:
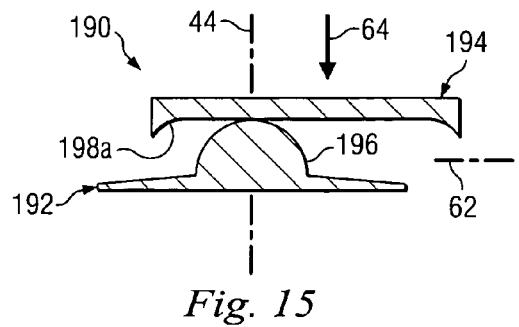
FIG. 15 is a cross sectional view of the assembled intervertebral assembly of the eighth embodiment of the current disclosure in a translated position.

Referring now to FIG. 13, an intervertebral disc prosthesis 190 may include two endplate assemblies 192, 194 which may be identical or substantially similar to endplate assemblies 24, 26 (FIG. 2) and therefore, will not be described in detail except to define a protrusion 196 corresponding to protrusion 32 of prosthesis 20, and a surface 198 corresponding to surface 34. As shown in FIG. 14, the prosthesis 190 may be assembled by positioning the protrusion 196 on the surface 198. The components, 192, 194 may be aligned along the longitudinal axis 62. The prosthesis 190 of this embodiment is one example of a relatively unconstrained joint (as compared to FIG. 10, for example). Protrusion 196 may be permitted to move unconstrained on surface 198 as the patient moves. The surface 198 may, in some embodiments as shown, have a slight lip 198a around the perimeter to provide a minimal amount of constraint. FIG. 15 shows the intervertebral disc prosthesis 190 in a translated position along, for example, an anterior-posterior axis 62. This embodiment, which may omit a bushing, center articulating portion, or other wear reduction device, may be suitable, for example, when contacting surfaces are formed of extremely durable material able to withstand point contact. This embodiment may also minimize stress on the adjacent vertebral endplates.

Figure 16:
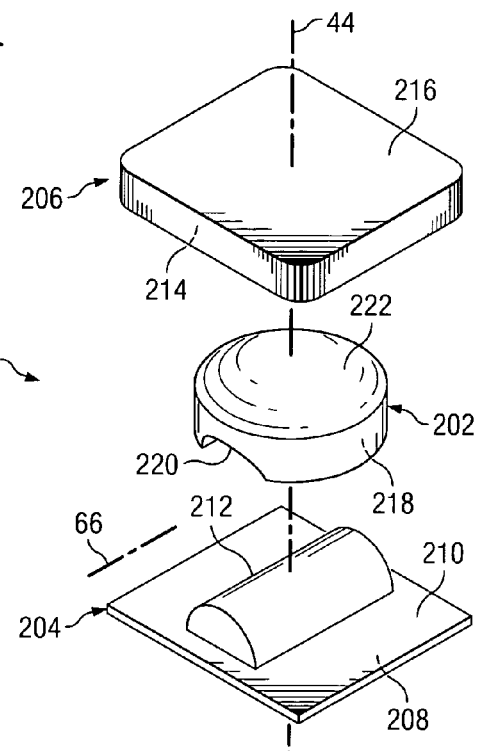
FIG. 16 is an exploded intervertebral assembly according to a ninth embodiment of the current disclosure.

Referring now to FIG. 16, a joint prosthesis 200, which in this embodiment may be an intervertebral disc prosthesis, includes a center member 202 interposed between two endplate assemblies 204, 206. The endplate assembly 204 may include an exterior surface 208 and an interior surface 210. A protrusion 212 may extend from the interior surface 210. In this embodiment, the protrusion 212 may be a semi-cylinder extended in the direction of axis 66, however, as described above, protrusions may be provided in a variety of shapes suitable for a particular application or particular location in the vertebral column. The surfaces 208 and 210 may be flat, angled, or curved. In this embodiment, the exterior surface 208 may be relatively flat or may be contoured to match the surface of an adjacent vertebral endplate. The interior surface 210 may taper away from the protrusion 212.

The endplate assembly 206 may include a interior surface 214 and an exterior surface 216. The surfaces 214 and 216 may be flat, angled, or curved. In this embodiment, the surface 216 may be generally flat or may be contoured to match the surface of an adjacent vertebral endplate. The interior surface 214 may be generally concave.

The center member 202 may vary somewhat in shape, size, composition, and physical properties, depending upon the particular joint for which the implant is intended. The shape of the center member 202 may complement that of the interior surfaces 210, 214 of the endplate assemblies 204, 206, respectively, to allow for a range of translational, flexural, extensional, rotational, and lateral bending motion appropriate to the particular joint being replaced. In this embodiment, the center member 202 may include a surface 218 having a cavity 220 generally conforming to the shape of the protrusion 212. The center member 202 may also have a surface 222 which, in this embodiment, may generally conform to the shape of the interior surface 214.

Figure 17:
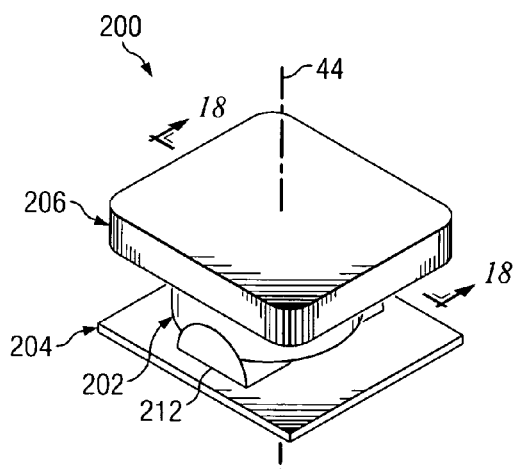
FIG. 17 is an assembled intervertebral assembly according to the ninth embodiment of the current disclosure.
Figure 18:
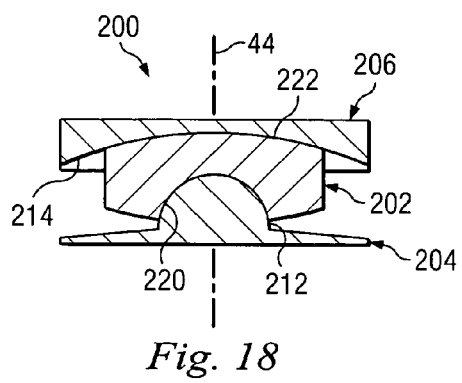
FIG. 18 is a cross sectional view of the assembled intervertebral assembly of the ninth embodiment of the current disclosure.

The components 202, 204, 206 may be formed from the same materials as described above for components 22, 24, 26, respectively. Referring now to FIGS. 17 & 18, the components of the intervertebral disc prosthesis 200 may be assembled by engaging the protrusion 212 with the cavity 220 and positioning the surface 222 of the center member 202 on the surface 214. The components 202-206 may be centrally aligned along the longitudinal axis 44. The intervertebral disc prosthesis 200 may be inserted in the void of the vertebral column 10 (of FIG. 1) created by discectomy. The positioning and functioning of the prosthesis 200 may be similar to that of the prosthesis 20 and therefore will not be described in detail. As described above for prosthesis 20, the prosthesis 200 may also have a bias to return toward a neutral position centrally aligned along the axis 44. Additionally, in this embodiment, the extension of the protrusion 212 in the lateral direction 66 may permit more stable and controlled lateral translation while decreasing the risk of dislodging the center member 202.

Figure 19:
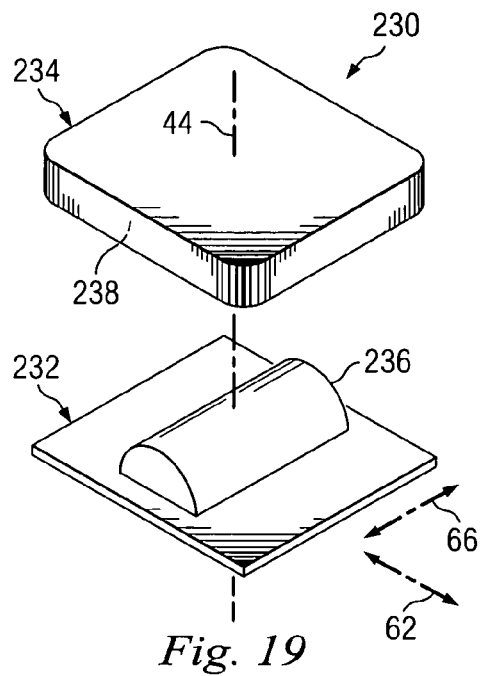
FIG. 19 is an exploded intervertebral assembly according to a tenth embodiment of the current disclosure.
Figure 20:
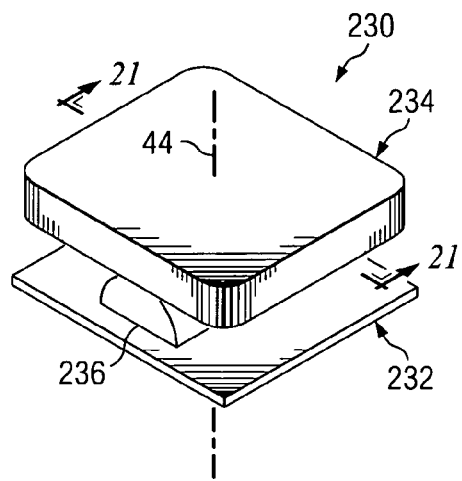
FIG. 20 is an assembled intervertebral assembly according to the tenth embodiment of the current disclosure.
Figure 21:
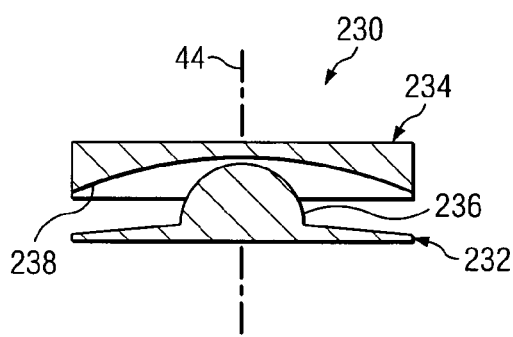
FIG. 21 is a cross sectional view of the assembled intervertebral assembly of the tenth embodiment of the current disclosure.

Referring now to FIG. 19, an intervertebral disc prosthesis 230 may include two endplate assemblies 232, 234 which may be identical or substantially similar to endplate assemblies 204, 206 (FIG. 16-18) and therefore, will not be described in detail except to define a protrusion 236 similar to protrusion 212 of prosthesis 200, and a surface 238 similar to surface 214. As shown in FIGS. 20 and 21, the prosthesis 230 may be assembled by positioning the protrusion 236 on the surface 238. The components 232, 234 may be centrally aligned along the longitudinal axis 44. The curved surface 238 and the curve of the protrusion 236 may provide constraint in the direction 62, but may provide relatively little constraint in direction 66. As shown, the protrusion may be relatively linear along the axis 66, but in other examples, the protrusion may be curved along the axis 66 to create an elliptical dome which provides constraint in both directions 62, 66. Prosthesis 230, which may omit a bushing, center articulating portion, or other wear reduction device, may be suitable, for example, when contacting surfaces are formed of extremely durable material able to withstand line contact.

Figure 22:
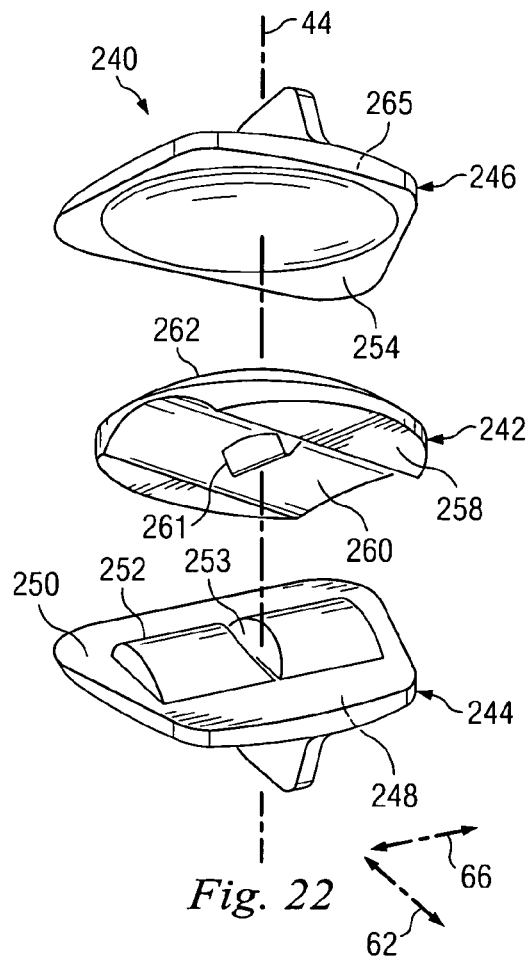
FIG. 22 is an exploded intervertebral assembly according to an eleventh embodiment of the current disclosure.

Referring now to FIG. 22, a joint prosthesis 240, which in this embodiment may be an intervertebral disc prosthesis, includes a center member 242 interposed between two endplate assemblies 244, 246. The endplate assembly 244 may include an exterior surface 248 and an interior surface 250. A protrusion 252 may extend from the interior surface 250. In this embodiment, the protrusion 252 may be a semi-cylinder extended along the direction of axis 66. A restraint member 253, which in this example may be a depression, may be formed on the protrusion 252 or the surface 250. The restraint member 253 may extend across the protrusion 252 in the anterior-posterior direction 62 and may be flared to permit limited motion in the lateral direction 66. The surfaces 248 and 250 may be flat, angled, or curved. In this embodiment, the exterior surface 248 may be relatively flat or may be contoured to match the surface of an adjacent vertebral endplate. The interior surface 250 may taper away from the protrusion 252.

The endplate assembly 246 may include a interior surface 254 and an exterior surface 256. The surfaces 254 and 256 may be flat, angled, or curved. In this embodiment, the surface 256 may be generally flat or may be contoured to match the surface of an adjacent vertebral endplate. The interior surface 254 may be generally concave.

The center member 242 may vary somewhat in shape, size, composition, and physical properties, depending upon the particular joint for which the implant is intended. The shape of the center member 242 may complement that of the interior surfaces 250, 254 of the endplate assemblies 244, 246, respectively, to allow for a range of translational, flexural, extensional, rotational, and lateral bending motion appropriate to the particular joint being replaced. In this embodiment, the center member 242 may include a surface 258 having a cavity 260 generally conforming to the shape of the protrusion 252. The cavity 260 may comprise a restraint mechanism 261 which, in this example, may be a boss. More than one restraint mechanism 261 may be used (corresponding to more than one restraint mechanism 253), and the one or more restraint mechanisms 261 may be located at alternative locations on center member 242. The boss 261 may extend across the cavity 260 in the anterior-posterior direction 62 to restrict motion along the axis 66, but in other examples a restraint mechanism may be positioned to restrict motion along the axis 62. The center member 242 may also have a surface 262 which, in this embodiment, may generally conform to the shape of the interior surface 254.

Figure 23:
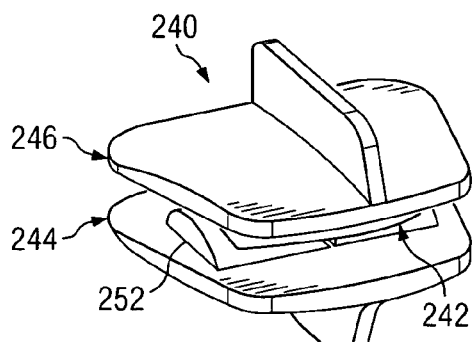
FIG. 23 is an assembled intervertebral assembly according to the eleventh embodiment of the current disclosure.
Figure 24:
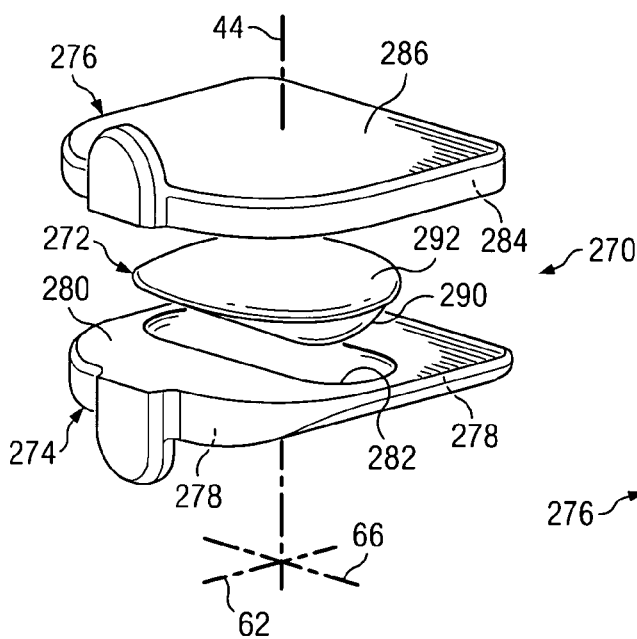
FIG. 24 is an exploded intervertebral assembly according to a twelfth embodiment of the current disclosure.
Figure 25:
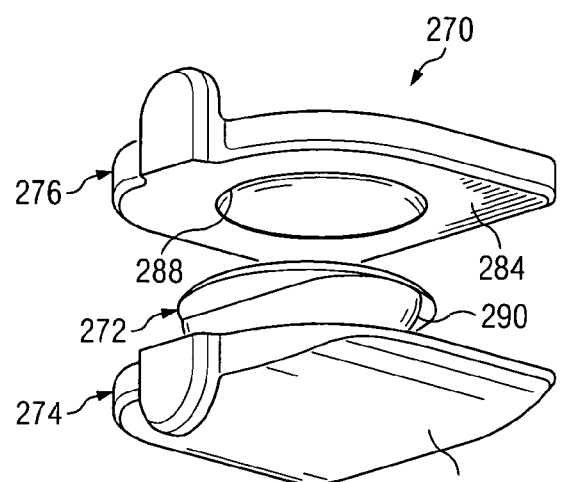
FIG. 25 is an exploded intervertebral assembly according to a twelfth embodiment of the current disclosure.

The components 242, 244, 246 may be formed from the same materials as described above for components 22, 24, 26, respectively. Referring now to FIG. 23, the components of the intervertebral disc prosthesis 240 may be assembled by engaging the protrusion 252 with the cavity 260 and further engaging the restraint mechanism 261 with the restraint member 253. The surface 262 of the center member 242 may be positioned on the surface 254. The components 242-246 may be centrally aligned along the longitudinal axis 44.

The intervertebral disc prosthesis 240 may be inserted in the void of the vertebral column 10 (of FIG. 1) created by the removal of disc 12. The positioning and functioning of the prosthesis 240 may be similar to that of the prosthesis 200 (FIG. 16) and therefore will not be described in detail. As described above in detail for prostheses 20 and 200, the prosthesis 240 may have a bias to return toward the neutral position aligned along the axis 44. Additionally, in this embodiment, the extension of the protrusion 252 in the lateral direction 66 may permit more stable and controlled lateral translation while decreasing the risk of dislodging the center member 242. The engagement of the restraint mechanism 261 and the restraint member 253 may limit lateral translation in accordance with the needs of a particular application. The lateral flare of the restraint member 253 may be varied such that embodiments having a narrow flare would permit less lateral translation than embodiments having wider flares. It is understood that a variety of other restraint mechanism 261/restraint member 253 configurations may be employed to restrict the amount of lateral translation. For example, the restraint member 253 can protrude to engage a grooved restraint mechanism 261.

Referring now to FIGS. 24-28, a joint prosthesis 270, which in this embodiment may be an intervertebral disc prosthesis, includes a center member 272 interposed between two endplate assemblies 274, 276. The endplate assembly 274 may include an exterior surface 278 and an interior surface 280. A depression 282, may be formed on the interior surface 280. In this embodiment, the depression 282 may be formed as a concave recess extended along the lateral direction of axis 66. The depression 282 may also be curved along the axis 66. The surfaces 278 and 280 may be flat, angled, or curved. In this embodiment, the exterior surface 278 may be relatively flat or may be contoured to match the surface of an adjacent vertebral endplate. The interior surface 280 may be generally flat around the depression 282.

The endplate assembly 276 may include a interior surface 284 and an exterior surface 286. The surfaces 284 and 286 may be flat, angled, or curved. In this embodiment, the surface 286 may be generally flat or may be contoured to match the surface of an adjacent vertebral endplate. The interior surface 284 may include a concave recess 288.

The center member 272 may vary somewhat in shape, size, composition, and physical properties, depending upon the particular joint for which the implant is intended. The shape of the center member 272 may complement that of the interior surfaces 280, 284 of the endplate assemblies 274, 276, respectively, to allow for a range of translational, flexural, extensional, rotational, and lateral bending motion appropriate to the particular joint being replaced. In this embodiment, the center member 272 may include a surface 290 generally conforming to the shape of the depression 282. The center member 272 may also have a surface 292 which, in this embodiment, may generally conform to the shape of the concave recess 288.

Figure 27:
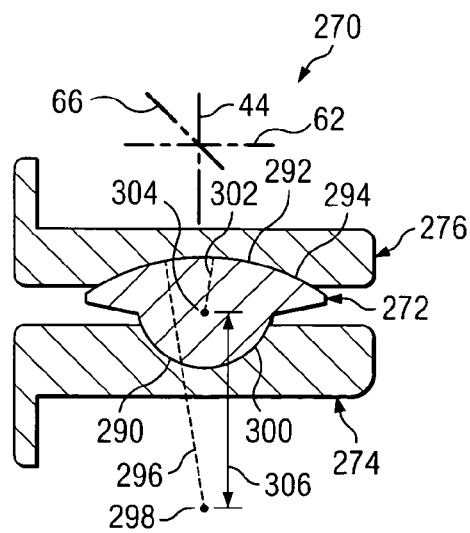
FIG. 27 is a cross-sectional view of the intervertebral assembly according to the twelfth embodiment of the current disclosure.

As shown in FIG. 27, the intervertebral disc prosthesis 270 may be in a neutral position when the components 272-276 are centrally aligned along the longitudinal axis 44. The surface 292 may have an arc 294 with a radius 296 and a center point 298. The surface 290 may have an arc 300 with a radius 302 and a center point 304. In the neutral position of FIG. 27, the center points 298, 304 are aligned along the longitudinal axis 44. In this example, the radius 302 is smaller than the radius 296, and accordingly, the arc 300 is tighter than the arc 294. A distance 306 extends between the center points 298, 304.

Figure 26:
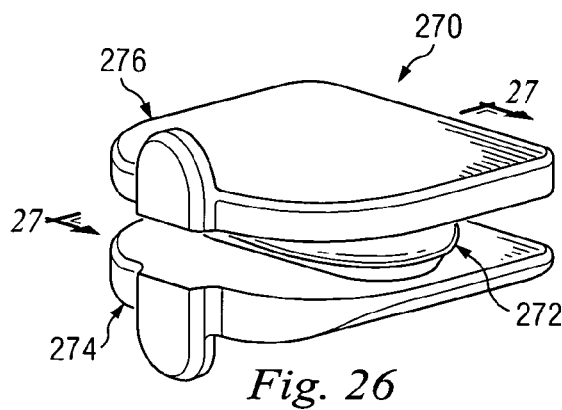
FIG. 26 is an assembled intervertebral assembly according to the twelfth embodiment of the current disclosure.
Figure 28:
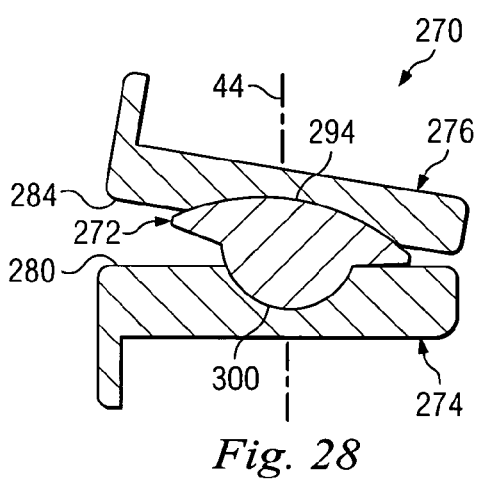
FIG. 28 is a cross-sectional view of the intervertebral assembly of the twelfth embodiment of the current disclosure in an articulated position.

The components 272, 274, 276 may be formed from the same materials as described above for components 22, 24, 26, respectively. Referring specifically to FIG. 26-28, the components of the intervertebral disc prosthesis 270 may be assembled by engaging the surface 290 with the depression 282 and further engaging the surface 292 with the surface 288. The components 272-276 may be centrally aligned along the longitudinal axis 44. The intervertebral disc prosthesis 270 may be inserted in the void of the vertebral column 10 (of FIG. 1) created by the removal of disc 12. The surface 278 may contact an endplate of vertebra 16 and the surface 286 may contact the endplate of vertebra 14.

Referring now to FIG. 28, the intervertebral disc prosthesis 270 may be articulated by, for example, flexion, extension, and/or translational movement. In response to this movement, the center member 272 may articulate between the endplate assembly interior surfaces 284, 280. With the position of the tighter arc 300 within the wider arc 294, the articulated prosthesis 270 may be constrained and biased to return to the more stable, neutral position aligned along the longitudinal axis 44 when subject to a load such as the patient's weight. This tendency of the prosthesis 270 to self align may allow more natural joint movement while preventing excessive translation that might otherwise result in the disassembly of the prosthesis 270. Further, this alignment bias may relieve excessive loads that might otherwise form in adjacent joints due to chronic over-displacement between the center points 298, 304. The depression 282 and the concave recess 288, in addition to permitting the smooth articulation of the center member 272, may function to limit or prohibit lateral movement along the axis 66. The matching curvatures of surfaces 282, 290 and 292, 288 may distribute the loadings and enhance the wear resistance of the components 272, 274, 276. The components 272, 274, 276 may be modular which may permit the selection of a center member 272 having a thickness which adjusts the prosthesis 270 to a desired height.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

What is claimed is:

1. An intervertebral implant comprising:
   a first member for engaging a first vertebra, the first member comprising a concave first surface, the concave first surface having a substantially constant first radius of curvature;
   a second member for engaging a second vertebra, the second member comprising a convex second surface and a tapered surface extending outwardly from the convex second surface, the convex second surface having a substantially constant second radius of curvature, the second radius of curvature being smaller than the first radius of curvature; and
   a center member positioned at least partially between the first member and the second member and in sliding articulating engagement with the first and second members, the center member comprising:
      a convex third surface for articulating with the concave first surface of the first member, the third surface having a substantially constant third radius of curvature substantially similar to the first radius of curvature,
      a concave fourth surface for articulating with the convex second surface of the second member, the concave fourth surface having a substantially constant fourth radius of curvature substantially similar to the second radius of curvature,
      a convex fifth surface extending substantially around the concave fourth surface, the convex fifth surface having a substantially constant fifth radius of curvature substantially equal to the first radius of curvature, the convex fifth surface configured for articulating with the tapered surface of the second member, the convex fifth surface being spaced from the tapered surface in a neutral position and in contact with the tapered surface in an articulation position, and
      a sidewall extending between the convex third surface and the convex fifth surface, the sidewall having a substantially circular outer profile;
   wherein the first member and the second member are formed of a relatively rigid biocompatible material and wherein the third and fourth surfaces of the center member are formed of an outer material that is harder than an inner material closer to a core of the center member.

2. The intervertebral implant of claim 1 wherein the convex second surface comprises a substantially semi-spherical protrusion.

3. The intervertebral implant of claim 1, wherein the first member and the second member are formed of a biocompatible metal.

4. The intervertebral implant of claim 1, wherein engagement of the convex fifth surface with the tapered surface of the second member in the articulation position limits the range of sliding articulating engagement between the center member and the second member.

5. The intervertebral implant of claim 1, wherein the first and second members are translatable with respect to one another via the sliding articulating engagement with the center member.

6. The intervertebral implant of claim 5, wherein engagement of the convex fifth surface with the tapered surface of the second member in the articulation position limits the range of translation between the first and the second members.

7. The intervertebral implant of claim 1, wherein the center member comprises the core positioned between the third and fourth surfaces formed of an elastomeric material.

8. An intervertebral implant comprising:
   a first member for fixedly engaging a first vertebral body, the first member comprising a first surface with a first curve defining a concave recess with a substantially circular boundary, the first curve having a first radius of curvature;
   a second member for fixedly engaging a second vertebral body, the second member comprising a second surface with a second curve defining a convex projection with a substantially circular boundary, the second curve having a second radius of curvature smaller than the first radius of curvature; and
   a center member positioned between the first member and the second member, the center member in sliding articulating engagement with the first and second members and comprising:
      a convex third surface for movably mating with the concave recess defined by the first curve of the first surface, the third surface having a third radius of curvature substantially similar to the first radius of curvature,
      a fourth surface having a concave central portion and a convex outer portion extending substantially around the concave central portion, the concave central portion for movably mating with the convex projection defined by the second curve of the second surface, the concave central portion having a substantially circular boundary and a fourth radius of curvature substantially similar to the second radius of curvature, and the convex outer portion having a fifth radius of curvature substantially similar to the first radius of curvature;
   wherein the first and second members are translatable with respect to one another via the sliding articulating engagement with the center member and wherein the first and second members are biased towards a central alignment where the first and second members are substantially aligned with one another;
   wherein the center member articulates with respect to the first and second members such that the convex outer portion of the center member is spaced from the second member in the central alignment and is in contact with a surface of the second member surrounding the convex projection in at least some articulation positions; and
   wherein the first member and the second member are formed of a relatively rigid biocompatible material and wherein the third and fourth surfaces of the center member are formed of an outer material that is harder than an inner material closer to a core of the center member.

9. The intervertebral implant of claim 8, wherein the third and fourth surfaces of the center member each have substantially circular outer boundaries.

10. The intervertebral implant of claim 9, wherein the circular outer boundary of the third surface is substantially similar to the circular outer boundary of the fourth surface.

11. The intervertebral implant of claim 10, wherein the center member further includes a sidewall extending between the convex third surface and the fourth surface.

12. The intervertebral implant of claim 11, wherein the sidewall is substantially cylindrical.

13. The intervertebral implant of claim 8 wherein the substantially circular boundary of the convex projection of the second member has a first diameter and wherein the substantially circular boundary of the concave central portion of the center member has a second diameter, the second diameter being less than the first diameter.

14. The intervertebral implant of claim 13, wherein the second member includes a tapered surface extending from the circular boundary of the convex projection and wherein engagement of the convex outer portion of the center member with the tapered surface of the second member limits the range of sliding articulating engagement between the center member and the second member.

15. The intervertebral implant of claim 14, wherein the convex outer portion of the center member is spaced from the tapered surface of the second member in the central alignment.

16. The intervertebral implant of claim 15, wherein the relatively rigid biocompatible material is selected from the group consisting of cobalt-chrome alloys, stainless steel, titanium alloys, alumina, and zirconia.

17. The intervertebral implant of claim 15, wherein the relatively rigid biocompatible material is selected from the group consisting of polycrystalline diamond, pyroltic carbon, polyetheretherketone (PEEK), ultra-high molecular weight polyethylene (UHMWPE), and cross-linked UHMWPE.

* * * * *